(12) United States Patent
Iwakura et al.

(10) Patent No.: US 11,324,809 B2
(45) Date of Patent: May 10, 2022

(54) METHOD OF PREVENTING AGGRAVATION OF A DISEASE INVOLVING A BIOLOGICAL MECHANISM CONTROLLED BY A DENDRITIC CELL IMMUNORECEPTOR

(71) Applicant: Tokyo University of Science Foundation, Tokyo (JP)

(72) Inventors: Yoichiro Iwakura, Tokyo (JP); Tomonori Kaifu, Sendai (JP)

(73) Assignee: Tokyo University of Science Foundation, Tokyo (JP)

( * ) Notice: Subject to any disclaimer, the term of this patent is extended or adjusted under 35 U.S.C. 154(b) by 150 days.

(21) Appl. No.: 16/611,883

(22) PCT Filed: May 14, 2018

(86) PCT No.: PCT/JP2018/018610
§ 371 (c)(1),
(2) Date: Nov. 8, 2019

(87) PCT Pub. No.: WO2018/207949
PCT Pub. Date: Nov. 15, 2018

(65) Prior Publication Data
US 2020/0261552 A1    Aug. 20, 2020

Related U.S. Application Data

(60) Provisional application No. 62/505,238, filed on May 12, 2017.

(51) Int. Cl.
*A61K 38/47* (2006.01)
*A61P 37/06* (2006.01)
*A61P 19/02* (2006.01)

(52) U.S. Cl.
CPC .............. *A61K 38/47* (2013.01); *A61P 19/02* (2018.01); *A61P 37/06* (2018.01); *C12Y 302/01018* (2013.01)

(58) Field of Classification Search
None
See application file for complete search history.

(56) References Cited

U.S. PATENT DOCUMENTS

| | | | |
|---|---|---|---|
| 8,273,357 B2 * | 9/2012 | Hacohen | A61K 47/61 424/193.1 |
| 10,792,300 B2 * | 10/2020 | Iwakura | C12N 5/0639 |
| 2009/0148432 A1 * | 6/2009 | Higuchi | A61P 9/10 424/94.61 |
| 2021/0040218 A1 * | 2/2021 | Iwakura | A61P 39/04 |

FOREIGN PATENT DOCUMENTS

| | | |
|---|---|---|
| JP | 2008-029319 A | 2/2008 |
| JP | 2009-019044 A | 1/2009 |
| WO | 2011105424 A1 | 9/2011 |
| WO | 2016006700 A1 | 1/2016 |

OTHER PUBLICATIONS

Homma T. et al. Recognition of Cell Surface GD3 by Monoclonal Antibody Anti-6C2 in Rheumatoid Arthritis Synovial Fluid. Arthritis & Rheumatism 44(2)296-306, Feb. 2001. (Year: 2001).*
Fujikado et al. "Dcir deficiency causes development of autoimmune diseases in mice due to excess expansion of dendritic cells" Nature Medicine, vol. 14, No. 2, pp. 176-180. Feb. 2008.
Jan. 28, 2020 (EP) Extended European Search Report Applicaiton No. 18799348.0.
Allergies: Current challenges and solutions Final Program Sep. 13-18, 2014 th 30 Symposiumof the collegium internationale allergologicum welcome, pp. 66-66.

* cited by examiner

*Primary Examiner* — Ralph J Gitomer
(74) *Attorney, Agent, or Firm* — Banner & Witcoff, Ltd.

(57) ABSTRACT

Provided are: a pharmaceutical composition for curing, treating, or preventing a disease involving a biological mechanism controlled by a dendritic cell immunoreceptor, in which the pharmaceutical composition contains a carbohydrate modifying enzyme as an active ingredient; and a method of curing, treating, or preventing a disease involving a biological mechanism controlled by a dendritic cell immunoreceptor.

5 Claims, 11 Drawing Sheets

Specification includes a Sequence Listing.

TRAP activity

*p<0.05, Mann-Whitney U test

SEQUENCE LISTING

```
<160> NUMBER OF SEQ ID NOS: 1

<210> SEQ ID NO 1
<211> LENGTH: 21
<212> TYPE: PRT
<213> ORGANISM: Artificial
<220> FEATURE:
<223> OTHER INFORMATION: MOG sequence

<400> SEQUENCE: 1

Met Glu Val Gly Trp Tyr Arg Ser Pro Phe Ser Arg Val Val His Leu
1               5                   10                  15

Tyr Arg Asn Gly Lys
            20
```

METHOD OF PREVENTING AGGRAVATION OF A DISEASE INVOLVING A BIOLOGICAL MECHANISM CONTROLLED BY A DENDRITIC CELL IMMUNORECEPTOR

RELATED APPLICATION DATA

This application is a National Stage Application under 35 U.S.C. 371 of PCT application number PCT/JP2018/018610 designating the United States and filed May 14, 2018; which claims the benefit of U.S. Provisional Application No. 62/505,238 and filed May 12, 2017 each of which are hereby incorporated by reference in their entireties.

TECHNICAL FIELD

The present disclosure relates to a pharmaceutical composition containing a carbohydrate modifying enzyme and a curing method using the pharmaceutical composition.

BACKGROUND ART

A dendritic cell immunoreceptor (Dendritic Cell Immunoreceptor, hereinafter also referred to as DCIR) is a membrane protein expressed in a cell such as a dendritic cell that is a major antigen-presenting cell, an osteoclast that is a bone-resorbing cell, and includes a domain (CRD) that recognizes a sugar chain in an extracellular region and an immunosuppressive signaling motif (ITIM) in an intracytoplasmic region. The inventors have previously succeeded in producing a mouse (Dcir−/−mouse) deficient in DCIR gene, and reported that the mouse spontaneously developed an autoimmune disease such as Sjögren syndrome or enthesitis with age (see, for example, Japanese Patent Application Laid-Open (JP-A) No. 2008-29319 and JP-A No. 2009-19044). The inventors have also reported that a Dcir−/− mouse is highly sensitive in collagen-induced arthritis, a model of autoimmune disease, which is due to excessive proliferation and differentiation of dendritic cells (see, for example, Fujikado et al., *Nat. Med.*, 2008).

As described above, DCIR is thought to play a role in negatively controlling osteoclast formation, dendritic cell differentiation/proliferation and production of inflammatory cytokines. Accordingly, if a ligand that specifically acts on DCIR is discovered, such a ligand is considered to be an effective means for suppressing or alleviating symptoms of osteometabolic diseases and autoimmune diseases. Since a dendritic cell plays a central role in an immune system, a therapeutic effect can be expected even in diseases such as allergies. Based on the above findings, the inventors have found that keratan sulfate-II (KS-II) signals into osteoclasts via SHP-1 as an endogenous ligand that specifically binds to DCIR (see, for example, WO 2011/105424). The inventors further found that asialo double-stranded N-type sugar chains having a specific chemical structure are ligands that specifically act on DCIR (see WO 2016/006700).

SUMMARY OF INVENTION

Technical Problem

Finding a large number of substances that specifically act on DCIR is beneficial in expanding range of choices of curing methods for diseases in which regulation of biological mechanisms controlled by DCIR can be effective.

Solution to Problems

In view of the above circumstances, the inventors provide the following.

<1> A pharmaceutical composition for curing, treating, or preventing a disease involving a biological mechanism controlled by a dendritic cell immunoreceptor, the pharmaceutical composition containing a carbohydrate modifying enzyme as an active ingredient.

<2> The pharmaceutical composition according to <1>, wherein the carbohydrate modifying enzyme is neuraminidase.

<3> The pharmaceutical composition according to <1> or <2>, wherein the disease is an osteometabolic disease, an autoimmune disease, or an allergic disease.

<4> The pharmaceutical composition according to any one of <1> to <3>, wherein the disease is rheumatoid arthritis or multiple sclerosis.

<5> The pharmaceutical composition according to any one of <1> to <4>, wherein the carbohydrate modifying enzyme is administered to a subject having the disease at an effective dose and interval for curing, treating, or preventing the disease.

<6> A method of curing, treating, or preventing a disease involving a biological mechanism controlled by a dendritic cell immunoreceptor, the method including administering an effective amount of a carbohydrate modifying enzyme to a subject in need of cure, treatment, or prevention of the disease.

<7> The method according to <6>, wherein the carbohydrate modifying enzyme is neuraminidase.

<8> The method according to <6> or <7>, wherein the disease is an osteometabolic disease, an autoimmune disease, or an allergic disease.

<9> The method according to any one of <6> to <8>, wherein the disease is rheumatoid arthritis or multiple sclerosis.

<10> The method according to any one of <6> to <9>, wherein the carbohydrate modifying enzyme is administered to a subject having the disease at an effective dose and interval for curing, treating, or preventing the disease.

<11> The method according to any one of <6> to <10>, wherein the administration is oral administration, subcutaneous administration, intraperitoneal administration, intramuscular administration, ophthalmic administration, ear drops administration, nasal administration, inhalation administration, transdermal administration, rectal administration, intrathecal administration, or intravenous administration. 33n <12> Use of a carbohydrate modifying enzyme for the manufacturing a pharmaceutical composition for curing, treating, or preventing a disease involving a biological mechanism controlled by a dendritic cell immunoreceptor.

<13> A carbohydrate modifying enzyme for use as a pharmaceutical composition for curing, treating, or preventing a disease involving a biological mechanism controlled by a dendritic cell immunoreceptor.

DESCRIPTION OF EMBODIMENTS

Figure 1:
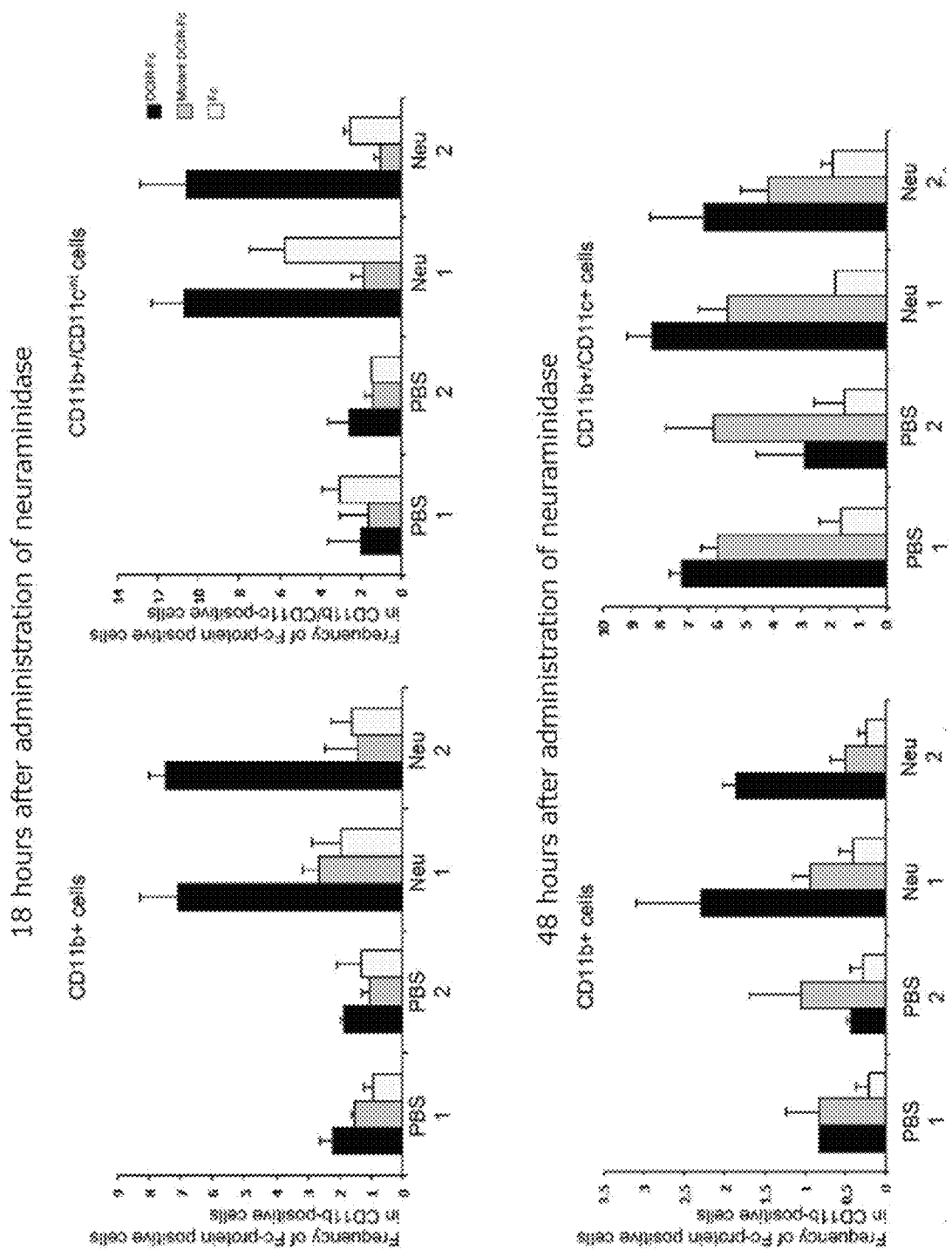
FIG. 1 shows the amount of DCIR ligand at 18 and 48 hours after administration of neuraminidase.

The inventors have found that when neuraminidase (Neuraminidase, EC 3.2.1.18), which is a glycosidase that cleaves a glycosidic bond of sialic acid, is administered to a wild type mouse that developed an experimental autoimmune disease, which is a model animal for multiple sclerosis as a carbohydrate modifying enzyme, a symptom of the disease is relieved, and calcium concentration in blood and activity of TRAP, which is an osteoclast marker is lowered by administration of neuraminidase. Since this effects of neuraminidase administration are not observed in C-type lectin receptor DCIR-deficient mice, it is considered that neuraminidase acts specifically in DCIR.

For example, this is supported by the following experiment: Neuraminidase was administered in vivo, and bone marrow cells were collected after 18 and 48 hours. A DCIR-Fc chimeric protein composed of an extracellular domain of DCIR and an Fc region of human IgG2 was bound to bone marrow cells, and an expression state of DCIR ligand was analyzed by FACS. As a result, binding of DCIR-Fc protein to bone marrow cells was increased.

This showed that bioligand of DCIR was exposed by administration of neuraminidase.

It was found that administration of neuraminidase to a mouse that induced collagen-induced arthritis, which is a model animal for rheumatoid arthritis that is another autoimmune disease improved clinical scores, improved histological severity, and decreased serum inflammatory cytokines.

It was found that administration of neuraminidase reduced serum calcium concentration and decreased the activity of tartrate-resistant acid phosphatase (TRAP), which is a marker for osteoclasts.

From these results, it was revealed that neuraminidase can be effectively used for the purpose of curing, treating, or preventing diseases or conditions involving biological mechanisms controlled by dendritic cell immunoreceptors.

In particular, neuraminidase can be suitably used for treatment of rheumatoid arthritis, multiple sclerosis, and osteoporosis.

<Pharmaceutical Composition>

The pharmaceutical composition of the disclosure contains a carbohydrate modifying enzyme as an effective ingredient. Examples of the carbohydrate modifying enzyme include neuraminidase, which is a glycosidase that cleaves a glycosidic bond of sialic acid. The finding that neuraminidase specifically acts on DCIR has not been reported.

Neuraminidase has an action of hydrolyzing $\alpha$-2,3-, $\alpha$-2,6-, and $\alpha$-2,8-glycosidic bond of sialic acid at the end of sugar chain. The strengths of $\alpha$-2,3 glucosidase activity, $\alpha$-2,6 glucosidase activity, and $\alpha$-2,8 glucosidase activity vary depending on an origin of neuraminidase, and any neuraminidase may be used. Those skilled in the art can find an appropriate dosage depending on a neuraminidase to be used.

A method of producing neuraminidase is not particularly limited, and examples thereof include collection from a living body, production by a genetic engineering method, and production by an organic synthetic chemical method. In particular, production by a genetic engineering method is advantageous for industrial production. A target neuraminidase can be easily produced by isolating a gene encoding neuraminidase from a neuraminidase-producing organism and recombining the gene into a host such as *Escherichia coli*. Examples of organisms that produce neuraminidase include, but are not limited to, *Clostridium perfringens, Arthrobacter urefaciens*, and influenza virus.

Humans are also known to produce four types of neuraminidase (or hNEUs 1 to 4). Use of neuraminidase derived from human is preferable from the viewpoint that immunogenicity is lowered when administered to human.

<Curing Method>

A method of curing, treating, or preventing of the disclosure (hereinafter, also simply referred to as "curing method") includes administering to a subject in need of cure, treatment, or prevention of a disease or a condition involving a biological mechanism controlled by a dendritic cell immunoreceptor (for example, a patient who is a human) a therapeutically, procedurally, or prophylactically effective amount of a carbohydrate modifying enzyme.

Specific aspects of a carbohydrate modifying enzyme to be administered to a patient and a carbohydrate modifying enzyme contained as an effective ingredient in the curing method of the disclosure can be the same as that described above as a specific aspect of a carbohydrate modifying enzyme contained in the pharmaceutical composition and effective ingredient of the disclosure.

When a carbohydrate modifying enzyme is administered to a subject in the curing method of the disclosure, a DCIR ligand exposed by the carbohydrate modifying enzyme selectively acts on DCIR in the subject living body. As a result, a biological mechanism controlled by DCIR can be intentionally adjusted. Examples of such a biological mechanism include osteoclast formation, dendritic cell proliferation, and cytokine production. Therefore, the method of the disclosure is effective as a method of curing a variety of osteometabolic diseases associated with excessive bone resorption and a variety of autoimmune diseases or allergic diseases associated with excessive immune reaction or inflammation due to production of an inflammatory cytokine. Furthermore, since the carbohydrate modifying enzyme acts specifically in a DCIR-dependent manner and suppresses functions of dendritic cells, osteoclasts, or the like, the enzyme can provide a curing method that can limit an action point of medicinal effect and has few side effects.

Examples of the osteometabolic disease include osteoarthritis, spondyloarthropathy, osteoporosis, Paget's disease, osteoarthritis, marble bone disease, and periodontal disease. Examples of autoimmune diseases include rheumatoid arthritis, multiple sclerosis, Guillain-Barre syndrome, Goodpasture syndrome, type I diabetes, thyroiditis, ulcerative colitis, and Sjögren syndrome. Examples of allergic diseases include bronchial asthma, atopic dermatitis, conjunctivitis, food allergy, anaphylaxis, contact dermatitis, allergic rhinitis, and chronic glomerulonephritis.

In the curing method of the disclosure, the method of administering the carbohydrate modifying enzyme of the disclosure to a subject is not particularly limited, and examples thereof include oral administration, subcutaneous administration, intraperitoneal administration, intramuscular administration, ophthalmic administration, ear drops administration, nasal administration, inhalation administration, transdermal administration, rectal administration, intrathecal administration, intravenous administration, or surgical treatment such as indwelling. The amount of a carbohydrate modifying enzyme to be administered to a subject and the administration interval are not particularly limited, and can be selected according to symptom type and condition, age and physique of the subject, DCIR activity status, intended degree of DCIR activation, type and amount of another ingredient used with the carbohydrate modifying enzyme or the like. Typically, a carbohydrate modifying enzyme is administered to a subject at doses and intervals that provide a therapeutically, procedurally, or prophylactically effective amount.

Example 1: Examination of Dose of Neuraminidase

Neuraminidase (0.2 U/mouse) (manufactured by Roche Ltd., derived from *Arthrobacter ureafaciens*) or PBS was intravenously administered to wild type 8-12 week-old mice via the tail vein, and bone marrow cells were collected 18 and 48 hours after the administration. Each of neuraminidase and PBS was administered to two mice, and the mice were designated as Neu1, Neu2, PBS1, and PBS2. DCIR-Fc was added and bound to the obtained bone marrow cells, and the ratio of the number of Fc positive cells to CD11b+ cells or the total number of cells of CD11b$^+$ and CD11c$^+$, which represent dendritic cells, was determined by FACS. DCIR-Fc is a chimeric protein composed of a mouse-derived DCIR extracellular domain (amino acid residues 208 to 689) and a human IgG2 antibody Fc domain. As a negative control, a mutant DCIR-Fc in which a mutation was inserted in a domain essential for sugar chain binding, and a protein of an Fc domain alone were used in place of DCIR-Fc. Neuraminidase 1U is defined as the amount of enzyme required to cleave 95% or more of terminal α-Neu5Ac from 1 nmol Neu5Acα2-3Galβ1-3GlcNAcβ1-3Galβ1-4Glc-AMC in 10 μL of a reaction solution at 37° C. for 5 minutes.

At 18 hours after administration of neuraminidase, binding of DCIR-Fc to dendritic cells was significantly increased compared to the negative control. However, after 48 hours, there was no significant difference in the Fc positive rate between DCIR-Fc and mutant DCIR-Fc (FIG. 1). Administration of neuraminidase is considered to increase the expression of DCIR ligand on the cell surface, and the effect is considered to decrease after 48 hours. Therefore, neuraminidase was administered once every two days.

Example 2: Calcium Concentration and Tartrate-Resistant Acid Phosphatase (TRAP) Activity of Serum after Administration of Neuraminidase Neuraminidase (0.1 U/mouse) (manufactured by Roche Ltd., derived from *Arthrobacter ureafaciens*) or PBS was intravenously administered to 8-12 week old male C57BL/6J strain wild type (WT) and DCIR knockout mice (Dcir−/−) five times every two days. 24 hours after the last administration, whole blood was collected by cardiac puncture under anesthesia. Next, serum was prepared, and the calcium ion concentration of the serum was measured using Calcium E-HA Test Wako (manufactured by FUJIFILM Wako Pure Chemical Corporation). The serum TRAP activity, which is a marker for osteoclasts, was measured by absorbance at a wavelength of 405 nm using TRACP & ALP Assay Kit (manufactured by Takara Bio Inc.) according to the instruction manual of the kit.

Figure 2A:
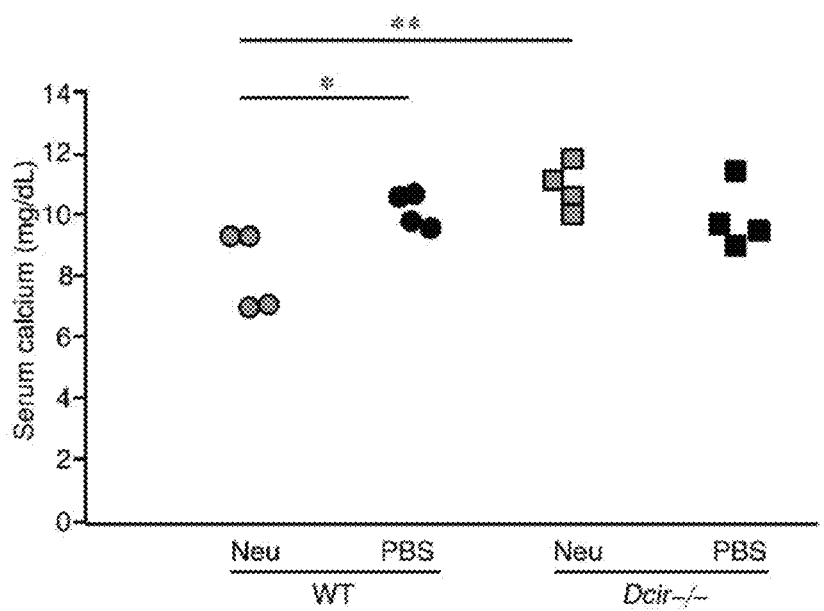
FIG. 2A shows changes in serum calcium concentration by administration of neuraminidase.
Figure 2B:
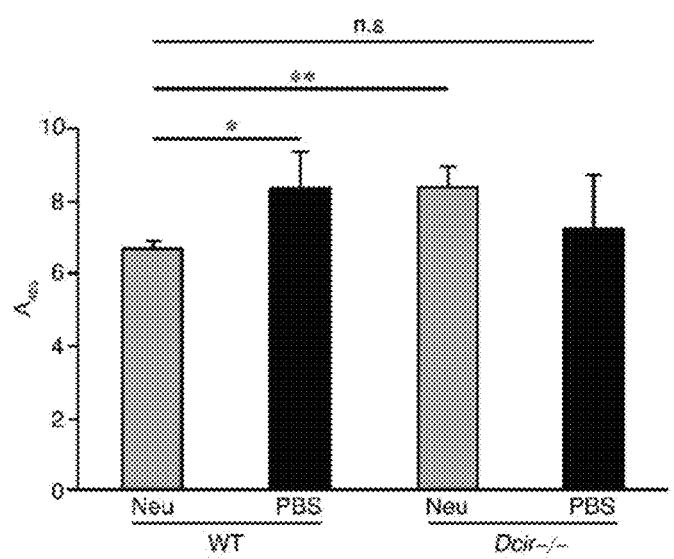
FIG. 2B shows changes in serum TRAP activity by administration of neuraminidase.

Serum calcium concentration and TRAP activity in wild type mice were significantly reduced ($p<0.05$) by administration of neuraminidase (FIGS. 2A and B). From this result, it was found that the activity of osteoclasts was suppressed by administration of neuraminidase. In DCIR knockout mice, administration of neuraminidase did not show a significant decrease in serum calcium concentration and TRAP activity, and therefore, neuraminidase is considered to act specifically on DCIR.

Example 3: Administration of Neuraminidase to Experimental Autoimmune Encephalomyelitis Mouse Experimental autoimmune encephalomyelitis is an animal model of multiple sclerosis. As experimental animals, C57BL/6J wild type and DCIR knockout mice (Dcir−/−) were used.

100 μg of MOG35-55 peptide (MEVGWYRSPFSRVVH-LYRNGK) was added to 100 μL of incomplete Freund's adjuvant (IFA) (manufactured by Thermo Fisher Scientific Inc.) and 100 μL of PBS solution of 500 μg of *Mycobacterium Tuberculosis* H37RA (manufactured by Difco Laboratories, Inc.) to obtain an emulsion. The resulting emulsion was injected subcutaneously on day 0 and day 7 with wild type and DCIR knockout mice to induce experimental autoimmune encephalomyelitis. On days 0 and 2, 200 ng/dose pertussis toxin was injected per mouse dissolved in PBS.

PBS solution of 100 μL neuraminidase (manufactured by Roche Ltd., derived from *Arthrobacter ureafaciens*) (wild type mice: n=6, DCIR knockout mice: n=7) or PBS (wild type mice: n=8, DCIR knockout mice: n=8) was intravenously administered 4 times at a dose of 0.1 units per mouse every 2 days from 7 days before the day of immunization with MOG (i.e. day 0). Neuraminidase or PBS was intravenously administered 4 times every 2 days in the same manner as described above from the day after day 0, namely, the day after the day of immunization with MOG.

Figure 3:
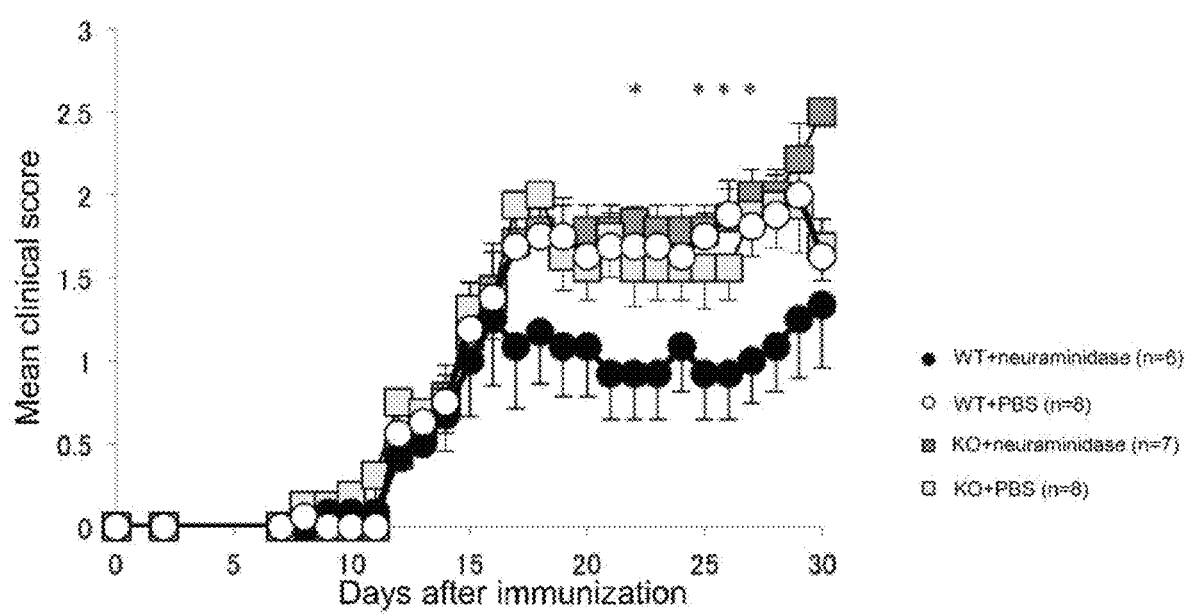
FIG. 3 shows an effect of administration of neuraminidase in wild type and DCIR knock-out mice that developed experimental autoimmune encephalomyelitis.

According to the following evaluation criteria, clinical scores of experimental autoimmune encephalomyelitis were observed daily on days 0, 2, and 7 to 30 to evaluate clinical scores. The results are shown in FIG. 3 and Table 1.

Clinical Score of Experimental Autoimmune Encephalomyelitis
0: No disease observed
0.5: Partial tail elevation failure
1: Tail paralysis
1.5: Paralysis of one hind limb
2: Paralysis of both hind limbs
2.5: weakness of one forelimb
3: weakness of both forelimbs
4: Paralysis of both forelimbs
5: Moribund An average score for each of the neuraminidase-administered group and the PBS-administered group was determined from the average score of all the mice in each group. A cumulative score is the sum of daily clinical scores of each mouse, and an average value was obtained for each group. A mean maximal score was calculated as the mean value per group of the maximal clinical score for each mouse.

Wild type mice that received neuraminidase had a significantly lower clinical score for EAE compared to the other groups (p<0.05). From this, it was found that administration of neuraminidase improved a clinical symptom of autoimmune encephalomyelitis. In DCIR knockout mice, no difference of the clinical score was observed between the PBS-administered group and the neuraminidase-administered group, and therefore, an effect of neuraminidase was considered to act specifically on DCIR.

TABLE 1

| EAE | Incidence | Mortality | Cumulative score | Maximum score | Week of onset |
|---|---|---|---|---|---|
| WT + Neu | 6/6(100%) | 0/6(0%) | 113 ± 11.6$^a$ | 1.58 ± 1.02$^b$ | 11.6 ± 1.36 |
| WT + PBS | 8/8(100%) | 0/8(0%) | 232 ± 7.26 | 2.31 ± 0.37 | 11.2 ± 1.75 |
| ΔDCIR + Neu | 7/7(100%) | 0/7(0%) | 214.5 ± 5.46 | 2.5 ± 0.0 | 12.5 ± 0.78 |
| ΔDCIR + PBS | 8/8(100%) | 0/8(0%) | 236 ± 8.90 | 2.27 ± 0.50 | 11.2 ± 1.48 |

Data are presented as means ± SD.
$^a$p = 0.066 (compared with WT + PBS),
$^b$p = 0.084 (compared with WT + PBS)

Example 4: Effect of Administration of Neuraminidase to Collagen-Induced Arthritis Mouse Collagen-induced arthritis is an animal model of rheumatoid arthritis. Collagen-induced arthritis mice (CIA mice) were prepared according to a previously reported method (Inglis J. J., Nat. Protocol., 2008). A summary of the method is described below. A powder of chicken type II collagen (IIC) (manufactured by Sigma-Aldrich Co. LLC.) was dissolved in a 10 mM aqueous acetic acid solution and allowed to stand at 4° C. overnight. An emulsion was prepared by mixing equal amounts of complete Freund's adjuvant (CFA) (manufactured by Difco Laboratories, Inc.) and chicken type II collagen aqueous acetic acid solution (4 mg/mL). Immunization was performed by intradermal administration of 100 μL of the obtained emulsion at three different locations near the tail root of 8-12 week old DBA/1J mice. On day 21 after the first immunization, the same amount of IIC/CFA emulsion was injected intradermally as a boost near the first administration site.

100 μL of a PBS solution of neuraminidase (Roche Ltd., derived from *Arthrobacter urefaciens*) (n=10) or PBS (n=10) was intravenously administered 4 times in such a manner that the dose was 0.1 units per mouse every 2 days from 7 days before the first immunization (i.e. day 0) with the above IIC/CFA emulsion. From 7 days before boosting, neuraminidase or PBS was intravenously administered 4 times every 2 days in the same manner as described above.

The arthritis score was evaluated for each limb according to the following criteria. The maximal value of arthritis score for one mouse (i.e. a score indicating the most severe) is 12.

According to the following evaluation criteria, the arthritis score was observed daily on days 0 and 21 to 45 to evaluate the arthritis score.

Arthritis Score 0: Normal 1: Slight swelling and/or redness 2: Severe swelling and/or redness 3: Joint stiffness An average score for each of the neuraminidase-administered group and the PBS-administered group was determined from the average score of all the mice in each group. A cumulative score is the sum of daily clinical scores of each mouse, and an average value was obtained for each group. A mean maximal score was calculated as the mean value per group of the maximal score for each mouse. The results are shown in FIG. 4. When the score of one individual was 1 or more, it was determined that the individual developed arthritis, and the ratio of the number of individuals who developed arthritis to the total number of individuals in each group was defined as the incidence.

Figure 4A:
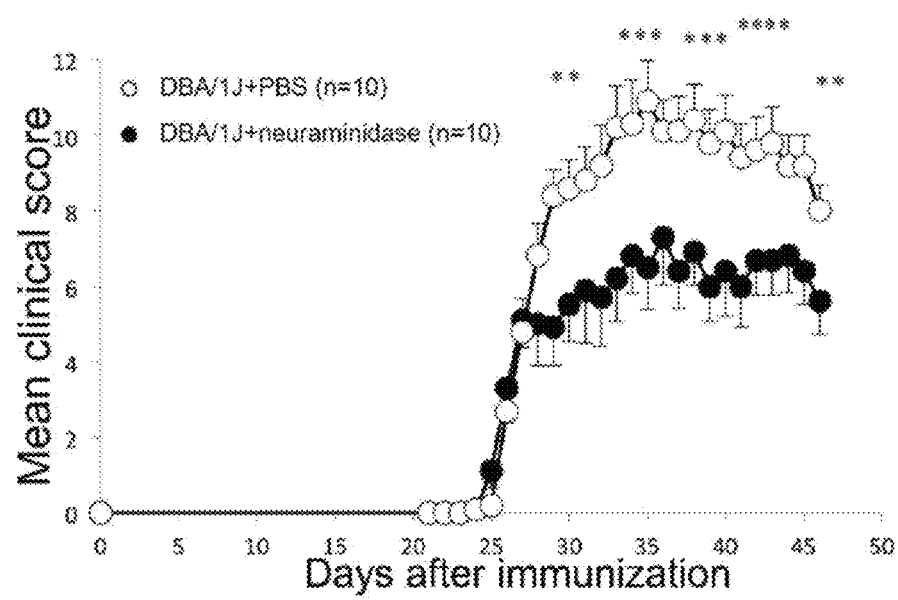
FIG. 4A shows an effect of administration of neuraminidase on arthritis scores in mice that developed collagen-induced arthritis.

FIG. 4A shows changes over time in the mean score of the neuraminidase-administered group and the mean score of the PBS-administered group. The neuraminidase-administered group consistently showed lower arthritis scores than the PBS-administered group after 26 days after the first immunization. It was shown that neuraminidase administration suppressed a clinical symptom of arthritis.

Figure 4B:
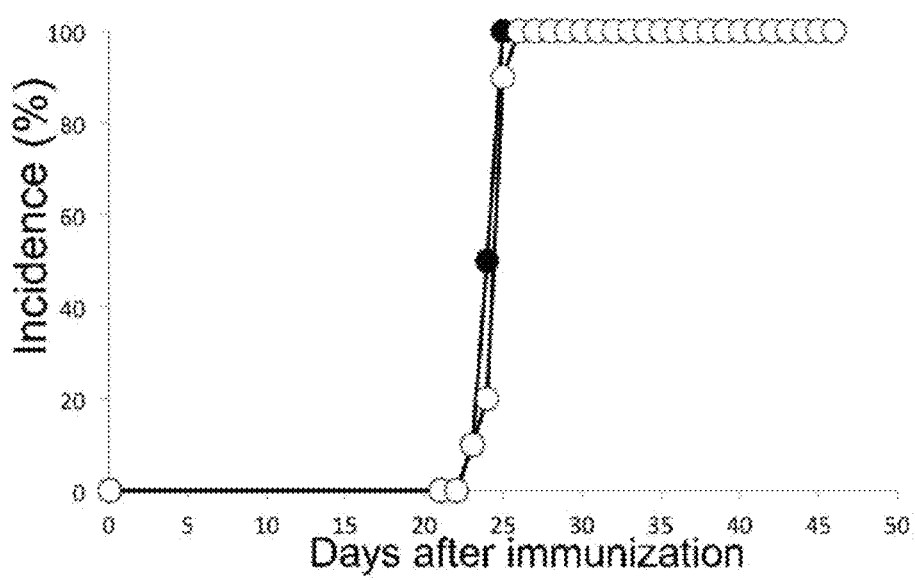
FIG. 4B shows the incidence of collagen-induced arthritis.

FIG. 4B shows the incidence of arthritis. On the 26th day after the first immunization, the incidence of arthritis was 100% in both the neuraminidase-administered group and the PBS-administered group.

Figure 4C:
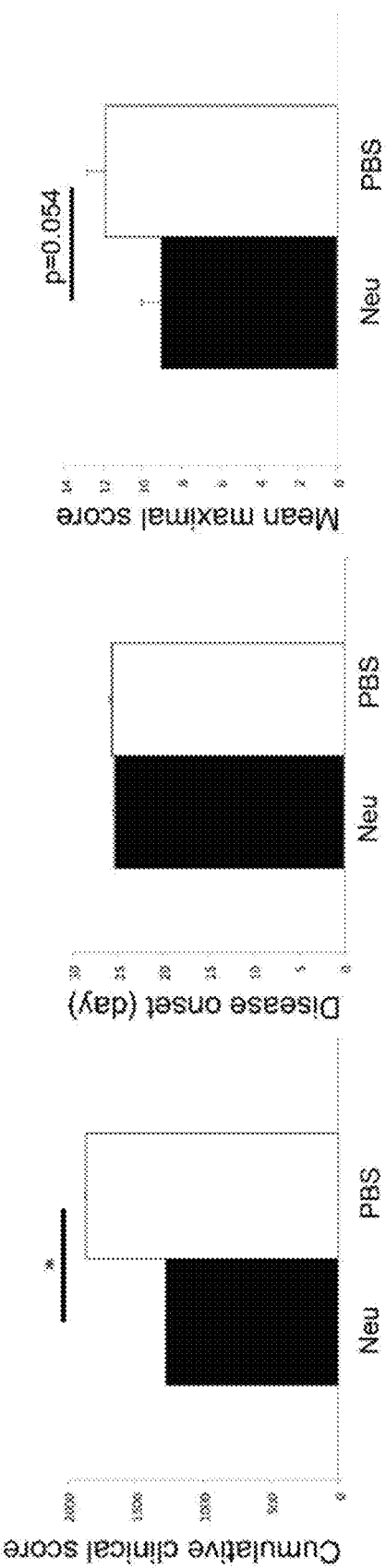
FIG. 4C shows an effect of administration of neuraminidase on arthritis scores in mice that developed collagen-induced arthritis.

FIG. 4C is comparison between the neuraminidase-administered group and the PBS-administered group regarding the cumulative arthritis score, onset date, and maximal score. The cumulative score was significantly lower in the neuraminidase-administered group than in the PBS-administered group ($p<0.05$), but there was little difference in the onset date. There was no significant difference in the maximum score, however, the p value was 0.054, indicating a boundary value.

<Reduction of Inflammatory Cytokines by Administration of Neuraminidase>

Blood was collected 45 days after the first immunization with IIC/CFA emulsion, and serum IFNγ, IL-17, and IL-6 were measured.

Using undiluted serum, the concentrations of IFN-γ and IL-17 were measured using a mouse ELISA set (manufactured by R&D Systems, Inc.), and the IL-6 concentration was measured using a mouse ELISA MAX (manufactured by Biolegend Inc.).

Figure 5:
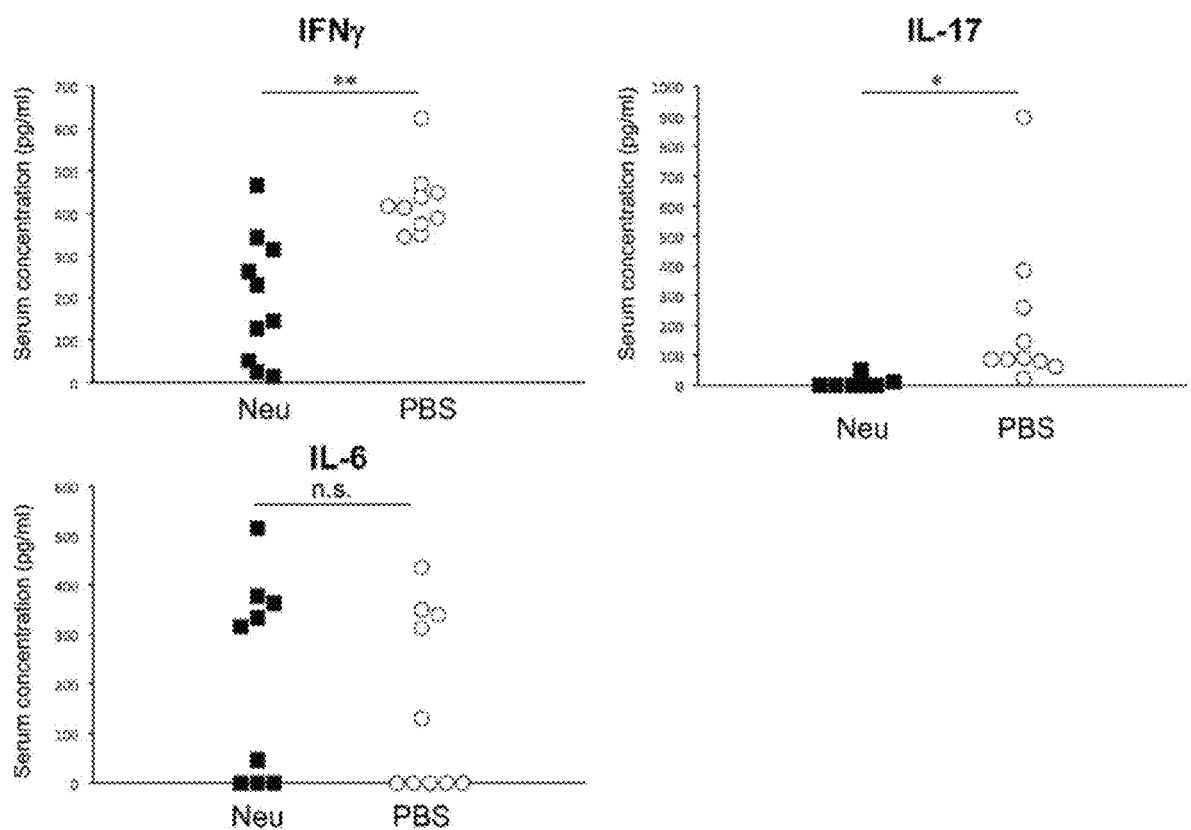
FIG. 5 shows reduction of inflammatory cytokines by administration of neuraminidase in mice that developed collagen-induced arthritis.

The results are shown in FIG. 5. IFNγ and IL-17 were significantly lower ($p<0.05$) in the neuraminidase-administered group than in the PBS-administered group. On the other hand, there was no significant difference in IL-6 between the two groups.

<Histological Evaluation of Severity of Arthritis>

Figure 6:
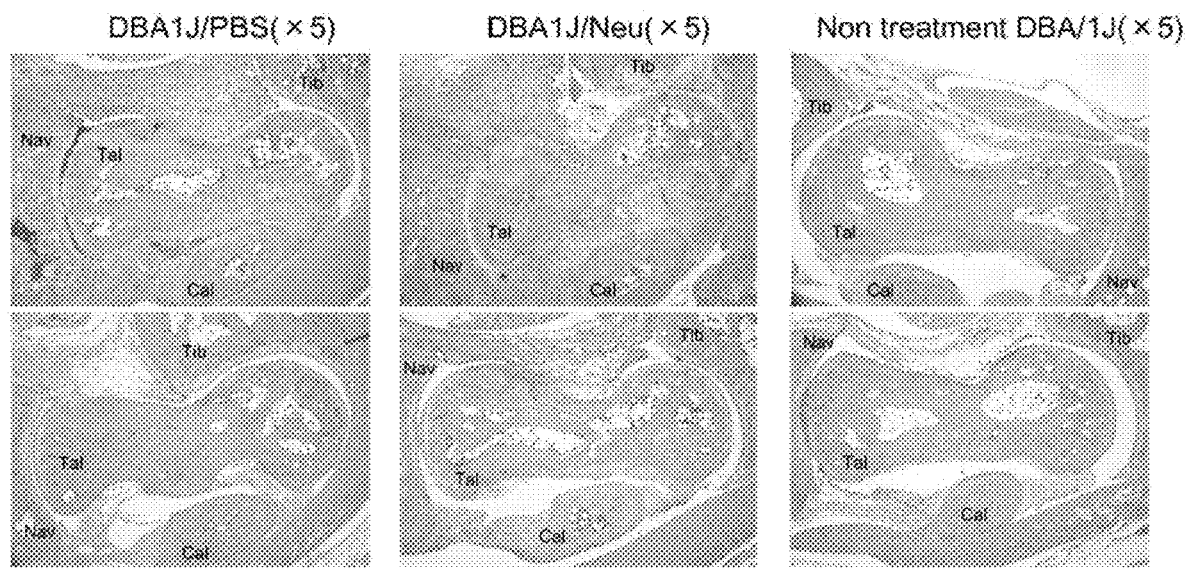
FIG. 6 shows a histological image of an ankle joint when neuraminidase was administered to a mouse that developed collagen-induced arthritis.

On day 45 after the first immunization with IIC/CFA emulsion, two ankle joints of hind limbs of a CIA mouse were cut under anesthesia. The joints were fixed with 10% neutral buffered formalin and subsequently decalcified in 10% EDTA. Two joints were embedded in a paraffin block, a 4 μm-thick paraffin section was prepared, and H & E staining was performed. A representative example of the H & E stained histological image of the ankle joint is shown in FIG. 6. In FIG. 6, Tal indicates the talus, Tib indicates the tibia, Cal indicates the calcaneus, and Nav indicates the navicular. In the neuraminidase-administered group and the PBS-administered group, inflammation of the ankle joint site with severe (upper) or mild (lower) bone destruction was observed, and in the neuraminidase-administered group, the state of inflammation was mild compared to the PBS-administered group. Bone destruction and inflammation were not observed in untreated mice.

The histological severity of arthritis was also assessed by scoring four parameters: inflammation, pannus formation, cartilage destruction, and bone destruction. The evaluation criteria for the score of each parameter are as follows.

Inflammation
0: Normal
1: Local infiltration of inflammatory cells was observed
2: Infiltration of inflammatory cells into a wide range of joint areas was observed
3: Extensive infiltration of inflammatory cells into a joint capsule was observed Pannus Formation
0: Normal
1: Pannus formation was observed in less than 2 locations
2: Pannus formation was observed at 2 locations or more and less than 4 locations
3: Pannus formation was observed in 4 or more locations
Note that, when wide-range pannus formation was observed in one location, the formation was counted as two locations for evaluation.

Figure 7:
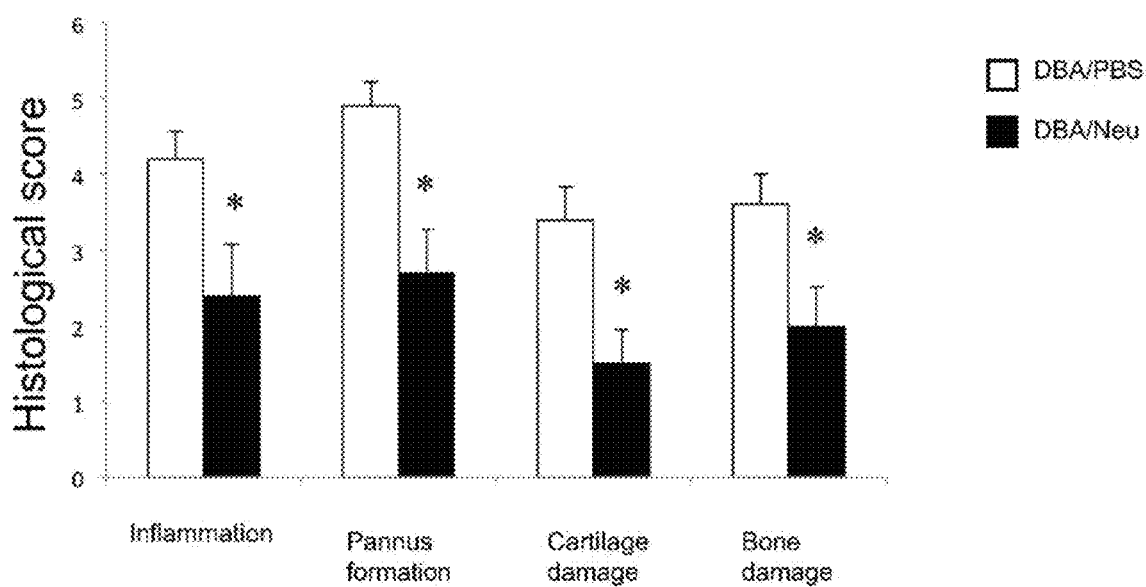
FIG. 7 shows results of scoring and evaluating histological images of ankle joints when neuraminidase was administered to mice that developed collagen-induced arthritis.

Cartilage Destruction
0: Normal
1: A small decrease in chondrocytes in the joint
2: Cartilage destruction in one area
3: Cartilage destruction in two or more areas Bone Destruction
0: Normal
1: Roughness of the surface of the talus was observed
2: Shallow destruction of the talus was observed
3: Deep destruction of the talus was observed FIG. 7 shows comparison between the score evaluation result of the neuraminidase-administered group and the score evaluation result of the PBS-administered group. In the neuraminidase-administered group, all of the four parameters of inflammation, pannus formation, cartilage destruction, and bone destruction showed significantly lower values than the PBS-administered group ($p<0.05$).

<Measurement of Anti-Collagen Antibody Titer>

On day 45 from the first immunization with IIC/CFA emulsion (or day 0), blood was collected from a mouse and serum was prepared. A 20 μg/mL chicken type II collagen PBS solution was dispensed into each well of a 96-well plate and allowed to stand overnight at 4° C. for coating. Subsequently, the chicken type II collagen solution was discarded, and PBS diluted with 10% fetal bovine serum was dispensed into each well and allowed to stand at room temperature for 1 hour for blocking. The serum was diluted with PBS to prepare a diluted sample of 5,000 times for total IgG measurement, 2,500 times for IgG1 measurement, and 500 times for IgG2a and IgG2b measurement. These diluted samples were dispensed into each well and incubated at room temperature for 2 hours. Subsequently, horseradish peroxidase-labeled goat anti-mouse IgG antibody (manufactured by Jackson ImmunoResearch Laboratories Inc.) or alkaline phosphatase-labeled mouse anti-mouse IgG1 antibody prepared to 0.8 μg/mL, alkaline phosphatase-labeled mouse anti-mouse IgG2a antibody, or alkaline phosphatase-labeled mouse anti-mouse IgG2b antibody (each manufactured by Santa Cruz Biotechnology, Inc.) prepared to 0.4 μg/mL was added and incubated at room temperature for 1 hour. Next, 3,3',5,5'-tetramethylbenzidine was used as a substrate for IgG antibody measurements, and p-nitrophenyl phosphate solution was used as a substrate for IgG1 antibody, IgG2a antibody, and IgG2b antibody measurement, and the color reaction was stopped with 1N HCl or 1N NaOH. The titer of each antibody was determined by measuring the absorbance at a wavelength of 450 nm for the total IgG antibody and the absorbance at a wavelength of 405 nm for other antibodies.

Figure 8:
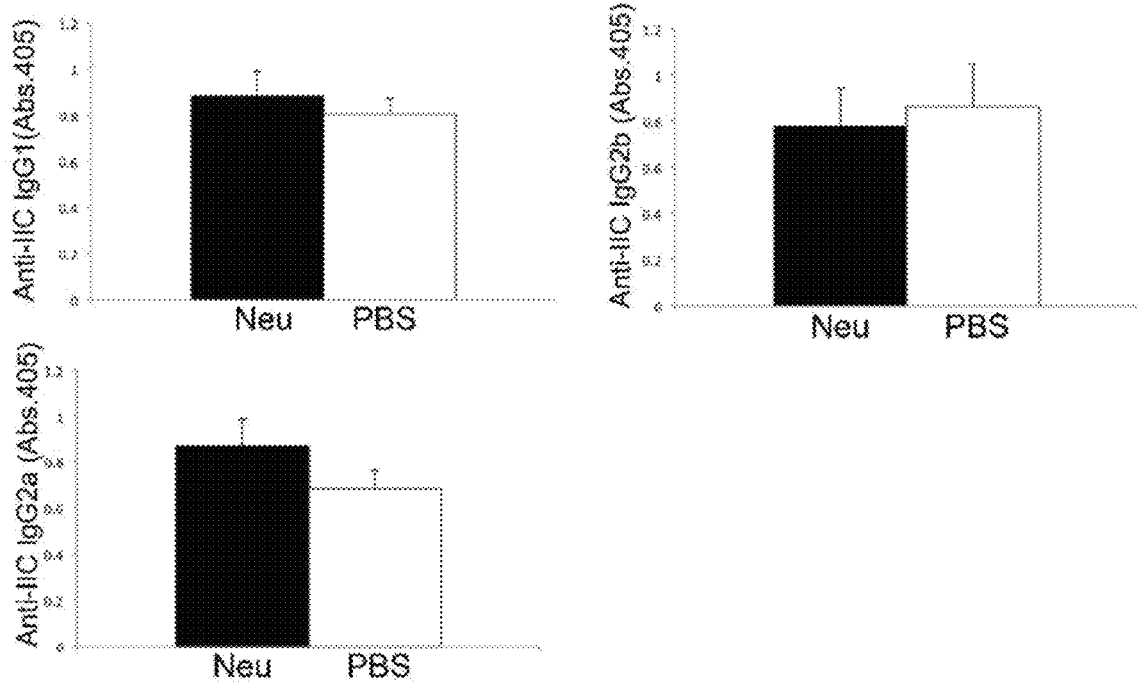
FIG. 8 shows the titers of anti-type II collagen IgG1 antibody, anti-type II collagen IgG2a antibody, and anti-type II collagen IgG2b antibody when mice that developed collagen-induced arthritis were administered neuraminidase.

The measurement results are shown in FIG. 8. As for the anti-type II collagen antibody, there was no difference in the titer of IgG1, IgG2a, and IgG2b antibodies between the neuraminidase-administered group and the PBS-administered group.

Example 5: Comparison of Neuraminidase Administration Effect to DCIR−/− and Wild Type Mice CIA was induced in DCIR−/− mice to examine whether the inhibitory effect of neuraminidase administration was exerted in a DCIR-dependent manner. 100 μL of a PBS solution of neuraminidase (manufactured by New England Biolabs Japan Inc., derived from *Clostridium perfringens*) (wild type mice: n=22, DCIR knockout mice: n=11) or PBS (wild type mouse: n=19, DCIR knockout mouse: n=14) was intravenously administered in such a manner to give a dose of 2 units per mouse. The neuraminidase of PBS was administered on the day before the first immunization (i.e. day 0) with IIC/CFA emulsion, followed by 6 doses every 2 days.

As described in Example 4, the arthritis score was evaluated and the histological severity was evaluated. The results are shown in FIGS. 9 to 12.

Figure 9:
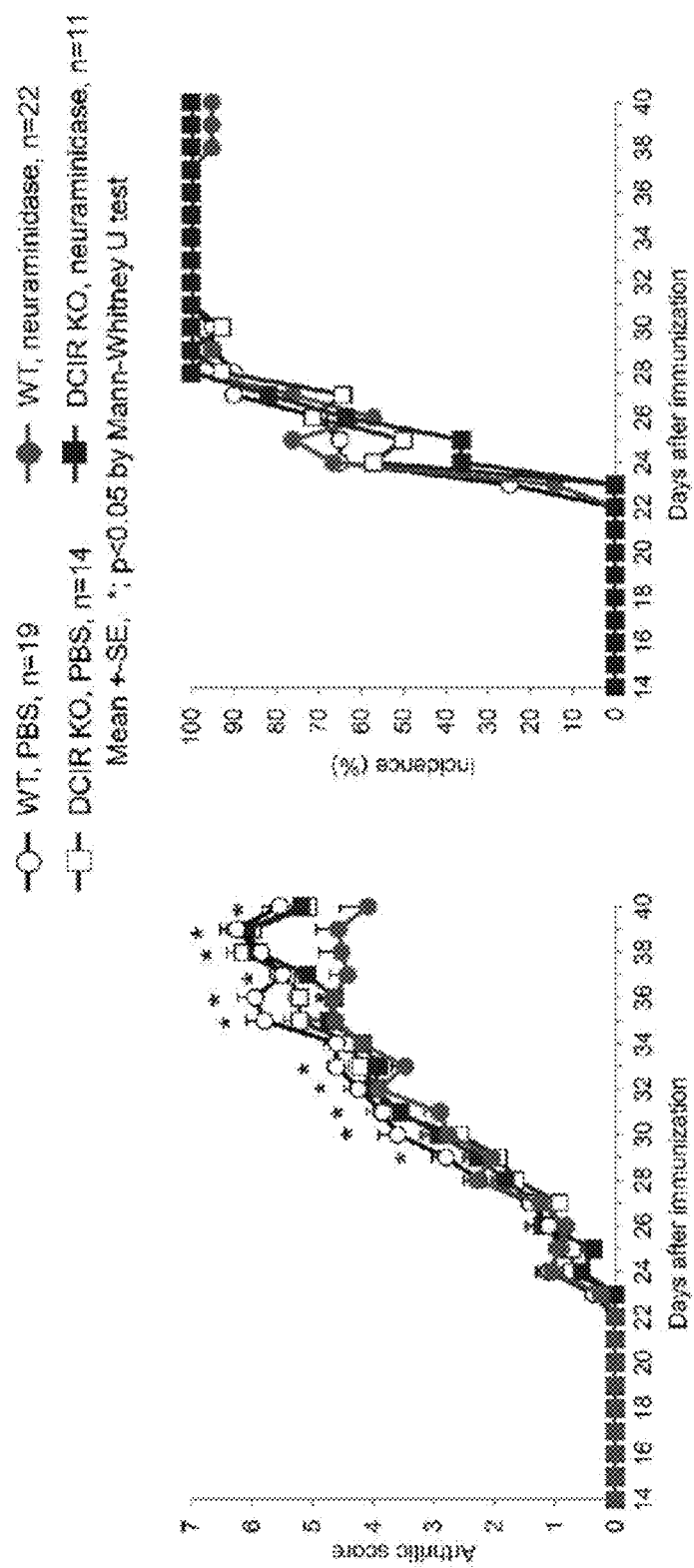
FIG. 9 shows comparison of changes over time in the arthritis score of DCIR−/− mice and that of wild type mice.
Figure 10A:
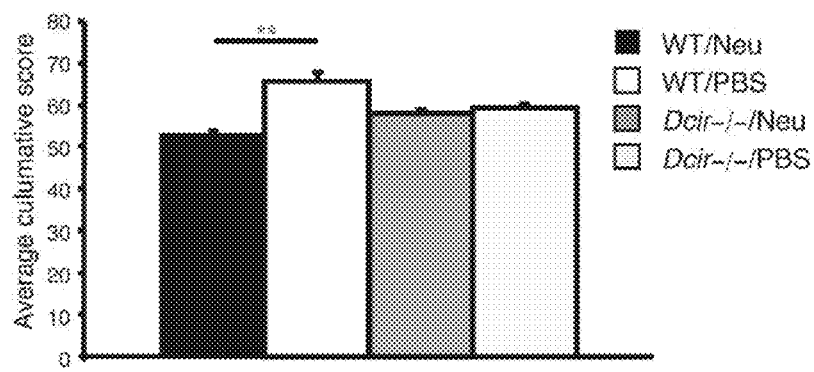
FIG. 10A shows comparison of cumulative arthritis scores between DCIR−/− mice and wild type mice.
Figure 10B:
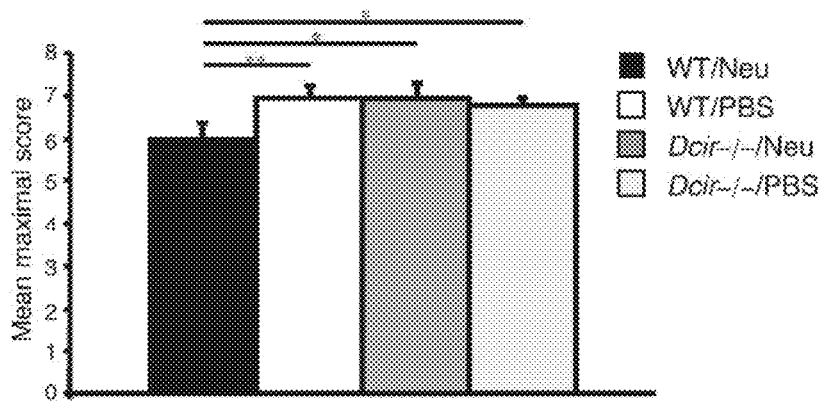
FIG. 10B shows comparison of the maximal score of arthritis score in DCIR−/− mice and the maximal score of arthritis score in wild type mice.
Figure 10C:
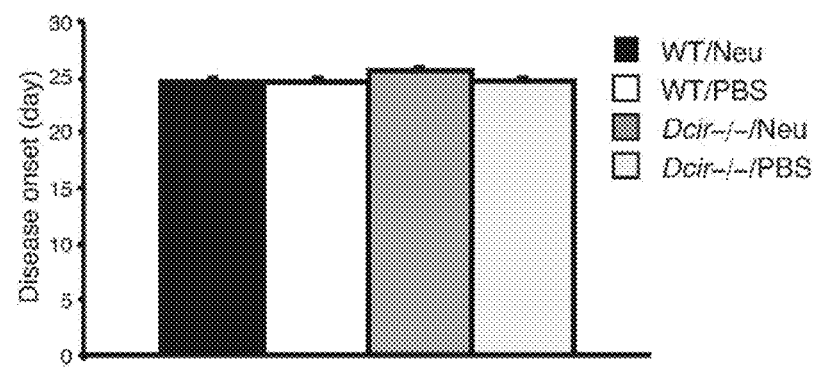
FIG. 10C shows comparison between the disease onset date of DCIR−/− mice and the onset date of wild type mice.

FIG. 9 shows comparison of changes over time in the arthritis score. FIG. 10A shows comparison of cumulative arthritis scores, FIG. 10B shows comparison of maximal scores, and FIG. 10C shows comparison of disease onset dates.

Wild type mice that received neuraminidase had significantly lower CIA arthritis scores compared to the other groups ($p<0.05$). Cumulative and maximal scores were significantly reduced ($p<0.05$) in wild type mice administered neuraminidase. There was no significant difference in the date of disease onset. On the other hand, in DCIR knockout mice, there was no difference between the cumulative score and the maximal score in the PBS-administered group compared to the neuraminidase-administered group.

From this, it was found that a clinical symptom of collagen-induced arthritis is improved by administration of neuraminidase. In DCIR knockout mice, there was no difference between the PBS-administered group and the arthritis score, and therefore, an effect of neuraminidase was considered to act specifically on DCIR.

Figure 11:
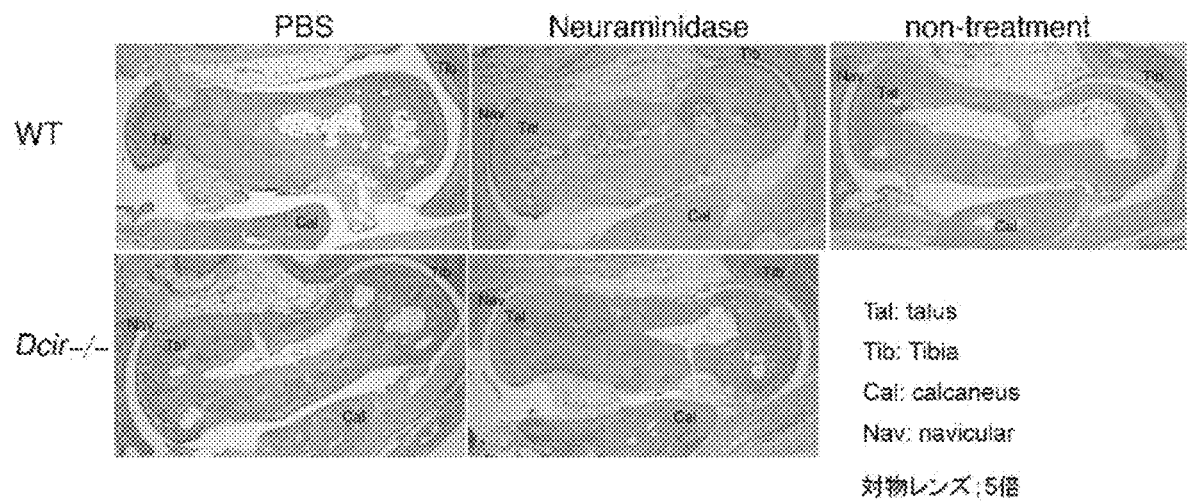
FIG. 11 shows H & E stained images of ankle joints of DCIR−/− mice and wild type mice.
Figure 12:
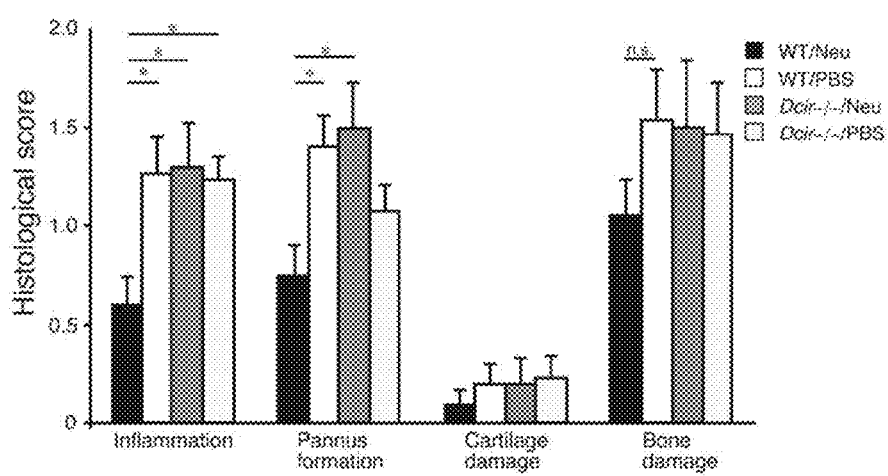
FIG. 12 shows a comparison of inflammation, pannus formation, cartilage destruction, and bone destruction between DCIR−/− mice and wild type mice.

FIG. 11 shows an H & E stained image of the ankle joint. FIG. 12 shows comparison of inflammation, pannus formation, cartilage destruction, and bone destruction.

In wild type mice, the neuraminidase-administered group reduced inflammation at an ankle joint site with bone destruction compared to the PBS-administered group. In DCIR knockout mice, there was no significant difference in inflammation between the neuraminidase-administered group and the PBS-administered group. In untreated mice, bone destruction and inflammation were not observed.

It was found through histological analysis that the scores of inflammation and pannus formation were significantly reduced in the neuraminidase-administered group. No significant difference was detected in the bone destruction score, but a notable decrease was observed. These differences were not observed in DCIR knockout mice, and therefore, an effect of neuraminidase was considered to act specifically on DCIR.

As described above, it has been shown that a carbohydrate modifying enzyme such as neuraminidase can cure, treat, or prevent a disease involving a biological mechanism controlled by a dendritic cell immunoreceptor.

The disclosure of U.S. Provisional Application No. 62/505,238, filed May 12, 2017, is hereby incorporated by reference in its entirety.

The invention is not limited to the description of the embodiments and Examples of the invention described above. Various modifications may be included in the invention as long as those skilled in the art can easily arrive at without departing from the description of the Claims.

All documents, patent applications, and technical standards herein are incorporated herein by reference to the same extent as if each individual document, patent application, and technical specification is specifically and individually indicated to be incorporated by reference.

The invention claimed is:

1. A method of preventing aggravation of a disease involving a biological mechanism controlled by a dendritic cell immunoreceptor, the method comprising administering an effective amount of a carbohydrate modifying enzyme to a subject in need of preventing aggravation of the disease, wherein the carbohydrate modifying enzyme is neuraminidase and wherein the disease is an osteometabolic disease or an autoimmune disease.

2. The method according to claim 1, wherein the disease is osteoporosis, rheumatoid arthritis, or multiple sclerosis.

3. The method according to claim 1, wherein the carbohydrate modifying enzyme is administered to a subject having the disease at an effective dose and interval for preventing aggravation of the disease.

4. The method according to claim 1, wherein the administration is oral administration, subcutaneous administration, intraperitoneal administration, intramuscular administration, ophthalmic administration, ear drops administration, nasal administration, inhalation administration, transdermal administration, rectal administration, intrathecal administration, or intravenous administration.

5. The method according to claim 1, wherein the disease is rheumatoid arthritis, or multiple sclerosis.

* * * * *